(12) United States Patent
Zadini et al.

(10) Patent No.: US 8,304,383 B2
(45) Date of Patent: *Nov. 6, 2012

(54) DISSOLUTION OF ARTERIAL PLAQUE

(75) Inventors: Filiberto Zadini, Camarillo, CA (US); Giorgio Zadini, Camarillo, CA (US)

(73) Assignee: AtheroNova Operations, Inc., Irvine, CA (US)

( * ) Notice: Subject to any disclaimer, the term of this patent is extended or adjusted under 35 U.S.C. 154(b) by 950 days.

This patent is subject to a terminal disclaimer.

(21) Appl. No.: 12/024,908

(22) Filed: Feb. 1, 2008

(65) Prior Publication Data

US 2008/0187569 A1  Aug. 7, 2008

Related U.S. Application Data

(63) Continuation-in-part of application No. 11/649,062, filed on Jan. 3, 2007, now abandoned, which is a continuation-in-part of application No. 11/384,150, filed on Mar. 17, 2006, now abandoned, which is a continuation-in-part of application No. 11/373,943, filed on Mar. 13, 2006, now abandoned, application No. 12/024,908, which is a continuation-in-part of application No. 11/542,694, filed on Oct. 4, 2006, now abandoned, and a continuation-in-part of application No. PCT/US2006/044619, filed on Nov. 16, 2006, and a continuation-in-part of application No. PCT/US2007/001214, filed on Jan. 16, 2007.

(60) Provisional application No. 60/739,143, filed on Nov. 22, 2005, provisional application No. 60/793,379, filed on Apr. 19, 2006, provisional application No. 60/930,410, filed on May 15, 2007, provisional application No. 60/760,471, filed on Jan. 20, 2006.

(51) Int. Cl.
*A61K 38/00* (2006.01)
*A61K 35/50* (2006.01)
*A61K 45/00* (2006.01)

(52) U.S. Cl. ............ 514/1.9; 424/528; 424/278.1

(58) Field of Classification Search ............ None
See application file for complete search history.

(56) References Cited

U.S. PATENT DOCUMENTS

| | | | |
|---|---|---|---|
| 3,053,255 A | 9/1962 | Meyer | |
| 4,602,003 A | 7/1986 | Malinow | |
| 5,446,070 A | 8/1995 | Mantelle | |
| 5,597,807 A | 1/1997 | Estrada et al. | |
| 5,837,282 A | 11/1998 | Fenske et al. | |
| 5,902,738 A | 5/1999 | Orsat et al. | |
| 6,165,500 A | 12/2000 | Cevc | |
| 6,423,742 B1 | 7/2002 | Larson | |
| 6,706,290 B1 | 3/2004 | Kajander et al. | |
| 6,780,849 B2 | 8/2004 | Herrmann et al. | |
| 6,849,257 B2 | 2/2005 | Grabowski et al. | |
| 2002/0052404 A1 | 5/2002 | Hunter et al. | |
| 2002/0091111 A1 | 7/2002 | Gilat | |
| 2003/0027833 A1 | 2/2003 | Cleary et al. | |
| 2003/0139385 A1* | 7/2003 | Song et al. | 514/182 |
| 2004/0143322 A1 | 7/2004 | Litvack et al. | |
| 2004/0151716 A1 | 8/2004 | Hamer et al. | |
| 2004/0267354 A1 | 12/2004 | Ringeisen et al. | |
| 2005/0070997 A1 | 3/2005 | Thornton et al. | |
| 2005/0158408 A1* | 7/2005 | Yoo | 424/728 |
| 2005/0163821 A1 | 7/2005 | Sung et al. | |
| 2005/0177225 A1 | 8/2005 | Hunter et al. | |
| 2005/0249770 A1 | 11/2005 | Hunter | |
| 2005/0261258 A1 | 11/2005 | Kolodney et al. | |
| 2005/0267407 A1 | 12/2005 | Goldman | |
| 2006/0111299 A1 | 5/2006 | Kisilevsky et al. | |
| 2006/0222695 A1 | 10/2006 | Zadini et al. | |
| 2007/0037203 A1 | 2/2007 | Kapeller-Libermann et al. | |
| 2007/0116754 A1 | 5/2007 | Zadini et al. | |
| 2007/0116755 A1 | 5/2007 | Zadini et al. | |
| 2007/0129425 A1 | 6/2007 | Zadini et al. | |
| 2007/0249543 A1 | 10/2007 | Zadini et al. | |
| 2008/0181927 A1 | 7/2008 | Zhao | |
| 2008/0187569 A1 | 8/2008 | Zadini et al. | |

OTHER PUBLICATIONS

Crosignani et al. Clinical Pharmacokinetics of Therapeutic Bile Acids, Clinical Pharmacokinetics, 30 (5) pp. 333-358. May 1996.*

Angelin et al., "Hepatic Uptake of Bile Acids in Man—Fasting and Postprandial Concentrations of Individual Bile Acids in Portal Venous and Systemic Blood Serum," J. Clin. Invest., The American Society for Clinical Investigation, Inc. vol. 70, Oct. 1982, pp. 724-731.

Ljubuncic et al., "Effect of deoxycholic acid and ursodeoxycholic acid on lipid peroxidation in cultured macrophages," Gut, 1996, vol. 39, pp. 478-478.

Marschall et al., "Isoursodeoxycholic acid: metabolism and therapeutic effects in primary biliary cirrhosis," Journal of Lipid Research, vol. 42, 2001, pp. 735-742.

Murphy et al., "Serum bile acids in primary bilary cirrhosis," Gut, vol. 13, 1972, pp. 201-206.

(Continued)

*Primary Examiner* — Michael G Hartley
*Assistant Examiner* — Nabila Ebrahim
(74) *Attorney, Agent, or Firm* — James W. Hill; McDermott Will & Emery LLP

(57) ABSTRACT

Embodiments of methods of treating atherosclerosis are described. In some embodiments an emulsifier is provided to achieve levels in the systemic circulation that are effective to solubilize atherosclerotic plaque, resulting in plaque regression. In some embodiments, levels of greater than 50 μM are achieved; in some embodiments levels ranging from about 100 μM to about 600 μM are achieved; in some embodiments, levels ranging from about 100 μM to about 300 μM are achieved. Emulsifiers can include bile salts, saponins, and ionic, nonionic, and zwitterionic detergents, or salts, conjugates, hydrates, solvates, or polymorphs thereof. In some embodiments, a statin can be administered simultaneously or sequentially with an emulsifier.

11 Claims, No Drawings

OTHER PUBLICATIONS

Nissen et al., "Effect of Very High-Intensity Statin Therapy on Regression of Coronary Atherosclerosis—The Asteroid Trial," JAMA, Apr. 5, 2006 (Reprinted), vol. 295, No. 13, pp. 1556-1565.

Ridlon et al., "Bile salt biotransformations by human intestinal bacteria," Journal of Lipid Research, vol. 47, 2006, pp. 241-259.

Sacquet et al., "Intestinal absorption, excretion, and biotransformation of hyodeoxycholic acid in man," Journal of Lipid Research, vol. 24, 1983, pp. 604-613.

Sehayek et al., "Hyodeoxycholic acid efficiently suppresses atherosclerosis formation and plasma cholesterol levels in mice," Journal of Lipid Research, vol. 42, 2001, pp. 1250-1256.

Tennent et al., "Plasma cholesterol lowering action of bile acid binding polymers in experimental animals,"Journal of Lipid Research, vol. 1. No. 5, 1960, pp. 469-473.

Williams et al., "Bioavailability of four ursodeoxycholic acid preparations," Aliment Pharmacol. Ther., 2000, vol. 14, pp. 1133-1139.

Ferri, et al., "Effect of S(-) perillic acid on protein prenylation and arterial smooth muscle cell proliferation," Biochemical Pharmacology, (2001), pp. 1637-1645, vol. 62, Elsevier Science Inc.

Phan, et al., "The *Diet1* Locus Confers Protection against Hypercholesterolemia through Enhanced Bile Acid Metabolism," The Journal of Biological Chemistry, Jan. 4, 2002, pp. 469-477, JCB Papers in Press.

Ellis, "Adjunt to Bile-Acid Treatment for Gall-Stone Dissoluation: Low-Dose Chenodeoxycholic Acid Combined With a Terpene Preparation", British Medical Journal, Feb. 21, 1981, vol. 282, pp. 611-612.

Rodriguez, "Low Density Lipoproteins downregulate Lysyl Oxidase in Vascular Endothelial Cells and the Arterial Wall", Arteriosclerosis, Thrombosis, and Vascular Biology, 2002, vol. 22, p. 1409-1414.

Sehayek, "Hyodeoxycholic Acid Efficiently Suppresses Atherosclerosis formation and Plasma Cholesterol Levels in Mice", Journal of Lipid Research, 2001, vol. 42, pp. 1250-1256.

Cohen-Solal et al., Effects of hyodeoxycholic acid and α-hyocholic acid, two 6 α-hydroxylated bile acids, on cholesterol and bile acid metabolism in the hamster, Biochimica et Biophysica Acta, vol. 1257; pp. 189-197 (1995).

M. Leuschner, et al., "Dissolution of Gall Stones With an Ursodeoxycholic Acid Mentol Preparation: A Controlled Prospective Double Blind Trial," Gut, 1988, vol. 29, pp. 428-432.

\* cited by examiner

DISSOLUTION OF ARTERIAL PLAQUE

RELATED APPLICATIONS

This application is a continuation-in-part of U.S. application Ser. No. 11/649,062, filed Jan. 3, 2007 now abandoned, entitled "Dissolution of Arterial Cholesterol Plaques by Pharmacological Preparation," which is a continuation-in-part of U.S. application Ser. No. 11/384,150, filed Mar. 17, 2006 now abandoned, entitled "Dissolution of Arterial Cholesterol Plaques by Pharmacological Preparation," which is a continuation-in-part of U.S. application Ser. No. 11/373,943, filed Mar. 13, 2006 now abandoned, entitled "Dissolution of Arterial Cholesterol Plaques by Pharmacological Preparation," which claims priority to U.S. Provisional Application No. 60/739,143, filed Nov. 22, 2005, entitled "Dissolution of Arterial Cholesterol Plaques by Pharmacological Preparation"; this application is also a continuation-in-part of U.S. application Ser. No. 11/542,694, filed Oct. 4, 2006 now abandoned, entitled "Dissolution of Arterial Cholesterol Plaques by Phytochemical Emulsifiers," which claims priority to U.S. Provisional Application No. 60/793,379, filed Apr. 19, 2006, entitled "Dissolution of Arterial Cholesterol Plaques by Phytochemical Emulsifiers"; this application also claims priority to U.S. Provisional Application No. 60/930,410, filed May 15, 2007, entitled "Dissolution of Arterial Cholesterol Plaques by Pharmacologically Induced Elevation of Endogenous Biliary Salts"; this application is also a continuation-in-part of International Application No. PCT/US2006/044619, filed Nov. 16, 2006, entitled "Dissolution of Arterial Cholesterol Plaques by a Class of Pharmacological Compounds," which claims priority to U.S. patent application Ser. No. 11/384, 150, filed Mar. 17, 2006, U.S. patent application Ser. No. 11/373,943, filed Mar. 13, 2006, and U.S. Provisional Application No. 60/739,143, filed Nov. 22, 2005; this application is also a continuation-in-part of International Application No. PCT/US2007/001214, filed Jan. 16, 2007, entitled "Drug-Eluting Stent with Atherosclerotic Plaques Dissolving Pharmacological Preparation," which claims priority to U.S. Provisional Application No. 60/760,471, filed Jan. 20, 2006, entitled "Drug-Eluting Stent with Atherosclerotic Plaque Dissolving Pharmacological Preparation"; the contents of all of the foregoing are hereby incorporated by reference herein in their entireties.

FIELD OF THE INVENTIONS

Embodiments described herein relate to pharmaceutical formulations comprising emulsifiers, for example, bile acids, detergents, and saponins, and pharmaceutically acceptable salts or conjugates of emulsifiers, and their use in the treatment of atherosclerosis, in particular the use of such pharmaceutical formulations to dissolve the lipid core of plaques to result in plaque regression.

BACKGROUND OF THE INVENTIONS

Cardiovascular disease is a leading cause of death in the human population. This is especially true in developed countries, where the increasing incidence of obesity is considered to be the major contributing factor to cardiovascular and related diseases. For example, the incidence of heart disease as a cause of death was 12.4% in all World Health Organization States, whereas in the U.S., heart attacks account for nearly 30% of deaths. In addition, other disease states related to or exacerbated by impairment of cardiovascular function make cardiovascular diseases the single greatest contributor to death and disability.

The underlying issue in cardiovascular disease is the development of atherosclerosis, a disease that affects vessels of the arterial circulation. It is characterized as a chronic inflammatory response in the walls of blood vessels, in part due to deposition of lipoproteins, in particular low density lipoproteins (LDLs), as well as infiltration by macrophages. Atherosclerosis is known to begin early in life (during childhood) with the rate of progression dependent on a variety of factors including diet, exercise, and genetic predisposition.

The earliest morphologically identifiable stage of plaque development is termed a fatty streak, which in fact is an accumulation of macrophages that have ingested oxidized LDL in the vessel wall, giving them the appearance of fat in the muscular tissue that forms the vessel wall. These macrophages ingest oxidized LDL in the plaque, accumulating numerous cytoplasmic vesicles—these macrophages become known as foam cells. Over time the fatty streak evolves to become an established plaque characterized by further accumulation of macrophages and the local accumulation of an inflammatory infiltrate. Eventually foam cells die, releasing their contents into the plaque, which further exacerbates the inflammatory reaction. In addition, cytokines released by damaged endothelial cells lead to smooth muscle proliferation and migration from the vessel media to the intima, leading to the development of a fibrous capsule that covers the plaque. Over time, calcification at the margins of the plaque can occur.

It has been known for some time that over time that progressive enlargement of atherosclerotic plaques eventually leads to a narrowing of the lumen of afflicted vessels. Traditionally, narrowing of 75% or greater has been considered clinically significant. However, more recently it has been discovered that events such as heart attacks can occur even when there is no sign of significant narrowing of vessels, due to the inherent instability of some plaques.

It is now known that plaques can be structurally unstable, and spontaneously rupture. When a plaque ruptures, tissue fragments and plaque contents are released into the lumen of the blood vessel, resulting in a clotting response. While the clot is effective to cover and stabilize the rupture, it intrudes into the lumen of the vessel, reducing luminal diameter, and obstructing blood flow, thus creating a stenotic region. If the compromise to flow is significant, for example where the clot completely or nearly completely occludes the lumen, ischemia can occur in tissues downs stream from the site of the blockage. Where the vessel is a coronary artery, this can lead to a myocardial infarction. Should the blockage occur in a cerebral artery stroke is possible. Significantly, the majority of fatal events occur from ruptures in areas where there is little prior narrowing, although it is recognized that over time repeated ruptures of plaques will lead to stenosis, and eventually downstream ischemia, with the same clinical outcome.

Because of the risk posed by unstable plaque, there is now a recognized need to detect atherosclerotic plaque, and in particular soft, or vulnerable plaque, prior to the patient becoming symptomatic. Earlier detection of vulnerable plaque can be especially useful in order to begin a course of treatment that can reduce the risk of a sudden ischemic event due to plaque rupture, or due to the gradual development of stenotic regions in a vessel as can occur over time, or to reopen areas of vessel that have become substantially occluded. Typically, treatment of stenosis in sensitive areas such as the heart or the brain has been accomplished by angioplasty techniques. Maintaining patency of vessels has become easier with the advent of vascular stent devices.

In the past, detection and diagnosis of atherosclerosis has been difficult. For example, according to data in the U.S. from 2004, the first symptom of cardiovascular disease in over half of those so diagnosed, is heart attack or sudden death. Unfortunately, by the time obvious symptoms arose, the disease is usually quite advanced with the result that treatment options and clinical outcome can be limited. The recognition of contributing factors such as the effect of cholesterol intake, obesity, and smoking, has led to an awareness of the benefit of preventative lifestyle choices in reducing the risk of developing atherosclerosis.

More recently, advances have also been made in both the diagnosis and treatment of cardiovascular disease. For example, 64 slice CT technology now makes it possible to evaluate the extent cardiovascular disease through detection of calcifications in vessels. In addition, CT protocols are also available that make it possible to visualize vulnerable plaque. Thus, it is becoming easier to detect atherosclerosis at earlier and earlier stages, providing an ever increasing window of opportunity to treat the disease at as early a stage as possible.

SUMMARY OF THE INVENTIONS

While prior art treatments can be effective to deal with some of the factors that contribute to the development of atherosclerotic plaque (e.g., use of statins to reduce cholesterol levels), or to open occlude vessel (e.g., angioplasty and vascular stents) there remains a need for effective ways in which to effect regression of existing plaques in order to decrease plaque burden in patients.

Accordingly, in some embodiments there is provided, a method, of treating atherosclerosis in a patient, comprising: administering, across an epithelium of a patient, a pharmaceutical formulation comprising an emulsifier; enhancing a permeability of the epithelium to the emulsifier with a permeability enhancer; wherein enhancing the permeability of the epithelium is effective to result in passage of the emulsifier across the epithelium and into the patient's systemic circulation; wherein the passage of the emulsifier across the epithelium results in sustained levels of the emulsifier in the patient's systemic circulation that are therapeutically effective to result in regression of an atherosclerotic plaque.

In some embodiments, the emulsifier comprises at least one of a bile acid, a saponin, a detergent, or pharmaceutically acceptable salts, conjugates, hydrates, solvates, polymorphs, or mixtures thereof. In some embodiments, the emulsifier comprises a bile acid, or pharmaceutically acceptable salts, conjugates, hydrates, solvates, polymorphs, or mixtures thereof.

In some embodiments, the sustained levels of the emulsifier in the systemic circulation are greater than 50 µM. In some embodiments, the sustained levels of the emulsifier in the systemic circulation are in a range between about 50 µM and about 600 µM. In some embodiments, the sustained levels of the emulsifier in the systemic circulation are in a range between about 100 µM and about 300 µM.

In some embodiments, the emulsifier comprises deoxycholic acid.

In some embodiments, the sustained levels of the deoxycholic acid in the systemic circulation are greater than 50 µM. In some embodiments, the sustained levels of the deoxycholic acid in the systemic circulation are in a range between about 50 µM and about 600 µM. In some embodiments, the sustained levels of the deoxycholic acid in the systemic circulation are in a range between about 100 µM and about 300 µM.

In some embodiments, the emulsifier comprises a mixture of ursodeoxycholic acid and deoxycholic acid in substantially equimolar amounts. In some embodiments, the emulsifier comprises hyodeoxycholic acid. In some embodiments, the sustained levels of the hyodeoxycholic acid in the systemic circulation are greater than about 50 uM. In some embodiments, the sustained levels of the hyodeoxycholic acid in the systemic circulation are in a range from about 50 uM to about 600 uM. In some embodiments, the sustained levels of the hyodeoxycholic acid in the systemic circulation are in a range from about 100 uM to about 300 uM.

In some embodiments, the permeability enhancer comprises at least one of a non-ionic detergent, an ionic detergent, and a zwitterionic detergent. In some embodiments, the permeability enhancer comprises at least one of iontophoresis, electroporation, sonophoresis, thermal poration, microneedle treatment, and dermabrasion.

In some embodiments, the pharmaceutical formation is administered intravenously. In some embodiments, the pharmaceutical formation is administered intra-arterially. In some embodiments, the pharmaceutical formation is administered orally. In some embodiments, the pharmaceutical formation is administered sublingually. In some embodiments, the pharmaceutical formation is administered transdermally. In some embodiments, the pharmaceutical formation is administered via an implantable device. In some embodiments, the pharmaceutical formation is administered by injection. In some embodiments, the pharmaceutical formation is administered transmucosally.

In some embodiments, the method further comprises administering a statin either simultaneously or sequentially with the pharmaceutical formulation. In some embodiments, the pharmaceutical formulation further comprises the statin.

In some embodiments, there is provided a method of treating atherosclerosis in a patient comprising: administering a pharmaceutical formulation comprising an emulsifier in an amount effective achieve a concentration of the emulsifier in the systemic circulation of at least 50 µM; wherein the concentration of the emulsifier in the systemic circulation is sustained for a period of at least two hours; wherein the concentration of the emulsifier is effective to result in regression of an atherosclerotic plaque.

In some embodiments, the emulsifier comprises at least one of a bile acid, a saponin, a detergent, or pharmaceutically acceptable salts, conjugates, hydrates, solvates, polymorphs, or mixtures thereof. In some embodiments, the emulsifier comprises a bile acid, or pharmaceutically acceptable salts, conjugates, hydrates, solvates, polymorphs, or mixtures thereof.

In some embodiments, the sustained levels of the emulsifier in the systemic circulation are greater than 50 µM. In some embodiments, the sustained levels of the emulsifier in the systemic circulation are in a range between about 50 µM and about 600 µM. In some embodiments, the sustained levels of the emulsifier in the systemic circulation are in a range between about 100 µM and about 300 µM.

In some embodiments, the emulsifier comprises deoxycholic acid. In some embodiments, the sustained levels of the deoxycholic acid in the systemic circulation are greater than 50 µM. In some embodiments, the sustained levels of the deoxycholic acid in the systemic circulation are in a range between about 50 µM and about 600 µM. In some embodiments, the sustained levels of the deoxycholic acid in the systemic circulation are in a range between about 100 µM and about 300 µM.

In some embodiments, the emulsifier comprises a mixture of ursodeoxycholic acid and deoxycholic acid in substantially equimolar amounts.

In some embodiments, the emulsifier comprises hyodeoxycholic acid. In some embodiments, the sustained levels of the hyodeoxycholic acid in the systemic circulation are greater than about 50 uM. In some embodiments, the sustained levels of the hyodeoxycholic acid in the systemic circulation are in a range from about 50 uM to about 600 uM. In some embodiments, the sustained levels of the hyodeoxycholic acid in the systemic circulation are in a range from about 100 uM to about 300 uM.

In some embodiments, the method further comprises the use of a permeability enhancer. In some embodiments, the permeability enhancer comprises at least one of a non-ionic detergent, an ionic detergent, and a zwitterionic detergent. In some embodiments, the permeability enhancer comprises at least one of iontophoresis, electroporation, sonophoresis, thermal poration, microneedle treatment, and dermabrasion.

In some embodiments, the pharmaceutical formation is administered intravenously. In some embodiments, the pharmaceutical formation is administered intra-arterially. In some embodiments, the pharmaceutical formation is administered orally. In some embodiments, the pharmaceutical formation is administered sublingually. In some embodiments, the pharmaceutical formation is administered transdermally. In some embodiments, the pharmaceutical formation is administered via an implantable device. In some embodiments, the pharmaceutical formation is administered by injection. In some embodiments, the pharmaceutical formation is administered transmucosally.

In some embodiments, the method further comprises administering a statin either simultaneously or sequentially with the pharmaceutical formulation. In some embodiments, the pharmaceutical formulation further comprises the statin.

In some embodiments, there is provided a method of treating atherosclerosis in a patient comprising: administering a pharmaceutical formulation comprising an emulsifier in an amount effective achieve a concentration of the emulsifier in the systemic circulation of at least 50 µM at five minutes after onset of administration; wherein the concentration of the emulsifier in the systemic circulation is sustained above 50 µM for a period of at least two hours; and wherein the concentration of the emulsifier is effective to result in regression of an atherosclerotic plaque.

In some embodiments, the sustained levels of the emulsifier in the systemic circulation are greater than 50 µM. In some embodiments, the sustained levels of the emulsifier in the systemic circulation are in a range between about 50 µM and about 600 µM. In some embodiments, the sustained levels of the emulsifier in the systemic circulation are in a range between about 100 µM and about 300 µM.

DETAILED DESCRIPTION OF THE INVENTIONS

One approach in the treatment of atherosclerosis has been to use pharmacologic agents to interfere with the synthesis of cholesterol, a component of LDL, a major component of the lipid core of the plaque. It is oxidized LDL that provides, at least in part, the primary insult to the vessel wall that results in infiltration of monocytes, their differentiation into macrophages, and the inflammatory reactions that ensues. For example, statins are now a drug of choice in the treatment of atherosclerosis on the basis of their ability to decrease cholesterol synthesis by interfering with the enzyme HMG-CoA reductase.

Other approaches have devised ways in which to stabilize plaques, so that the risk of rupture and the attendant possibility of an acute coronary event is minimized or removed. Other approaches include treating plaque locally with anti-thrombolytics in order to prevent the complications due to clot formation after plaque rupture, for example as disclosed in International Patent Application No. PCT/IN2006/000037 (Chandrasekar).

Despite the relatively widespread use of statins to treat atherosclerosis, at the normally prescribed doses these compounds only reduce but do not eliminate the risk of acute coronary events due to atherosclerotic plaque. As a result, there remains a need to a way in which to reduce plaque volume in patients, in essence to reverse the progression of atherosclerosis, by causing the regression of existing plaques.

U.S. Pat. No. 7,141,045 (Johansson et al.) discloses a method of dissolving plaque by direct application of a dissolution fluid through an intravascular catheter. The dissolution fluid can include a variety of detergents, surfactants, and other solubilizing agents, in addition to enzymes, and metal ion chelators. While such an approach might be useful for acute treatment of known atherosclerotic lesions, it is seriously limited in it utility. First, the procedure is invasive, such that it can only be performed by a surgeon in an operating room situation. This necessarily means the procedure will be costly. Second, the treatment is only effective for plaques that can be effectively reached by catheter, and only for plaques whose location is known well enough by imaging techniques, such that the catheter can be guided to the desired location. Local treatment is thus generally ineffective as a sole method for the systemic treatment of atherosclerotic plaque.

As a result, there remains a need for non-invasive, systemically effective compositions and treatments that we effective to result in solubilization and regression of atherosclerotic plaque, especially soft, or vulnerable, plaque. Results from prior studies, testing whether statins were effective to cause plaque regression, have been described as equivocal. For example, in the recently completed ASTEROID study (Nissen et al., (2006), JAMA 295: 1556-1565), experiments were designed to test whether 40 mg/day of rosuvastatin would be effective to result in a decrease in plaque volume, as evidenced by intravascular ultrasound imaging techniques. While the treatment was particularly effective at modulating LDL, HDL, and triglyceride levels, plaque volume after 2 years was only reduced by 8.5% (SD=13.7) in the most diseased segments of vessels examined, and by only 6.7% (SD=11.1) with respect to normalized total atheroma volume. Thus, statins are not particularly effective at producing significant reductions in plaque burden, even when provided at twice the normally prescribed dosage for a period of two years.

Embodiments of the present invention use emulsifiers provided either systemically or locally to dissolve plaque and result in plaque regression. Emulsifiers can include bile salts, saponins, and various detergents.

Bile acids are cholesterol-derived organic acids that have detergent properties. Bile acids play important roles physiologically in the absorption, transport, and secretion of lipids. These compounds have been characterized as primary or secondary bile acids, depending on whether they are synthesized de novo (primary) or are derived by subsequent chemical modification (secondary). Primary bile acids are produced by the liver and include cholic acid ($3\alpha,7\alpha,12\alpha$-trihydroxy-$5\beta$-cholanic acid) and chenodeoxycholic acid ($3\alpha,7\alpha$-dihydroxy-$\beta$-cholanic acid). Dehydroxylation of the primary bile acids, for example by intestinal bacteria, produces the more hydrophobic secondary bile acids, for example deoxycholic acid (3α,12α,-dihydroxy-5β-cholanic acid), and lithocholic acid (3α-hydroxy-5β-cholanic acid). Together, the primary and secondary bile acids make up about 99% of the total bile acid pool in humans.

The role of circulating bile acid levels in the development of atherosclerosis is not clear in the prior art. Previous studies in animal model systems have suggested that lowering circulating levels of bile acids through the use of bile acid sequestrants lowers LDL levels and results in regression of atherosclerotic plaque (Wissler, *J. Clin. Apher.* 4: 52-58, 2006). The bile acid sequestrants colesevelam HCl has been shown to reduce LDL particle number and increase LDL particle size in patients with hypercholesterolemia (Rosenson, *Atheroscl.* 185: 327-330, 2006). Dietary supplements comprising bile acid polymeric organic bases have been shown to inhibit cholesterol rise and atherosclerotic plaque formation in chickens on a high cholesterol diet (Tennent et al., *J. Lip. Res.* 1: 469-473, 1960). Thus, collectively the prior art suggests that decreasing circulating bile acid levels should be effective to reduce progression, or even promote regression of atherosclerotic plaques.

Contrary to these prior art studies, where reducing circulating levels of bile salts is predicted to slow or regress plaque, embodiments of the present disclosure teach formulations and methods that lead to a sustained increase in the level of emulsifiers in the systemic circulation. These levels are effective to dissolve the lipid components of atherosclerotic plaque, especially vulnerable plaque, leading to plaque regression. In some embodiments, the emulsifiers comprise bile acids. In some embodiments, the emulsifiers are detergents, for example, ionic detergents, nonionic detergents, and zwitterionic detergents. In some embodiments, the emulsifiers comprises saponins. In some embodiments, the emulsifiers comprise combinations of bile acids, detergents, and/or saponins. Experimental examples described below demonstrate that bile salt emulsifiers can be effective to dissolve the lips core of atherosclerotic plaque.

There are instances where the concentration of bile acids have been increased systemically. For example, it has been previously shown that feeding hyodeoxycholic acid (HDCA) to C57BL/6 LDL r-KO knockout mice (genetically predisposed to develop atherosclerosis) results in a reduced rate of formation of atherosclerotic plaque relative to mice not provided HDCA (Sehayek et al., *J. Lip. Res.* 42: 1250-1256, 2001). Plasma levels of wild-type mice, provided the same amount of dietary HDCA, ranged up to about 50 μM. However, there is no evidence that these levels were effective to result in plaque regression, as is provided by the embodiments described herein.

Primary biliary cirrhosis (PBC) is an inflammatory disease characterized by destruction of the small bile ducts within the liver, eventually leading to cirrhosis. While the cause of PBC is not precisely known, the presence of auto-antibodies in PBC patients suggests an autoimmune origin. Among the various symptoms that arise as a result of PBC, it is known that total plasma cholesterol tends to be elevated, by as much as 50%. Despite the increases in cholesterol levels, however, it appears that PBC patients are not at an increased risk of atherosclerosis. In addition, it has been shown that PBC patients have elevated levels of bile acids (Murphy et al., *Gut* 13: 201-206, 1972), with levels averaging about 200 μM, as compared to normal levels which are less than 10 μM. Thus, embodiments as described herein are effective to mimic the high levels of bile salts observed in PBC patients, and in doing so are effective to result in regression of atherosclerotic plaque.

In general, the effective dose of a emulsifier that is effective to result in regression of atherosclerotic plaque will vary depending on a number of factors. Influential variable can include for example, the patient's individual processing of bile salts or other emulsifiers in the circulation, their personal diet and exercise regime, as well as other genetic and environmental factors. The specific optimal dosage for any particular emulsifier can vary from compound to compound, and can depend on variations in chemical properties of one emulsifier as compared to another. For example different emulsifiers can have differing $p_{Ka}$ values, or solubility, which will in turn affect how a patient metabolizes the compound, how much can remain in the circulation, and how effective the compound will be in terms of solubilizing the lips component of atherosclerotic plaques.

Thus in some embodiments, an effective dose will be that which is sufficient to result in sustained levels of a emulsifier, for example, a bile acid, of at least about 50 μM. In some embodiments, the effective dose is sufficient to result in sustained levels of a emulsifier in a range from about 100 μM to about 600 μM. In some embodiments, the effective dose is sufficient to result in sustained levels of a emulsifier in a range from about 100 μM to about 300 μM. By sustained levels, it is meant that the levels of the emulsifier are maintained in the systemic circulation for a period of at least about 2 hours. In some embodiments, by sustained, it is meant that the levels of the emulsifier are maintained in the systemic circulation for at least 24 hours.

Examples of Bile Acid Emulsifiers

As used herein, the term "bile acid" is meant to include bile acids, pharmaceutically acceptable salts, and conjugates of bile acids, or said salts. Examples of bile acids useful in embodiments as described herein can include, without limitation any naturally occurring or synthetically produced bile acid, salt, or conjugate thereof, having the ability to solubilize the lipid component of atherosclerotic plaque. This can include cholic acid, chenodeoxycholic acid, deoxycholic acid, lithocholic acid, ursodeoxycholic acid, hyodeoxycholic acid, and any conjugate or pharmaceutically acceptable salt thereof.

In addition, bile acids useful in embodiments of formulation for use as described herein can include, without limitation: 1,3,12-trihydroxycholanoic acid; 1,3,7,12-tetrahydroxycholanoic acid; 3beta-hydroxy-delta 5-cholenic acid; 3 beta-hydroxychol-3-en-24-oic acid; 3'-isothiocyanatobenzamidecholic acid; 3,12-dihydroxy-5-cholenoic acid; 3,4,7-trihydroxycholanoic acid; 3,6,12-trihydroxycholanoic acid; 3,7,12,23-tetrahydroxycholan-24-oic acid; 3,7,12-trihydroxy-7-methylcholanoic acid; 3,7,12-trihydroxycoprostanic acid; 3,7,23-trihydroxycholan-24-oic acid; 3,7-dihydroxy-22,23-methylene-cholan-24-oic acid (2-sulfoethyl) amide; 3-((3-cholamidopropyl)dimethylammonium)-1-propanesulfonate; 3-((3-deoxycholamidopropyl) dimethylammonio)-1-propane; 3-benzoylcholic acid; 3-hydroxy-5-cholen-24-oic acid 3-sulfate ester; 3-hydroxy-7-(hydroxyimino)cholanic acid; 3-iodocholic acid; 7,12-dihydroxy-3-(2-(glucopyranosyl)acetyl)cholan-24-oic acid; 7,12-dihydroxy-3-oxocholanic acid; allocholic acid; chapso; chol-3-en-24-oic acid; cholanic acid; sodium cholate; methyl cholate; benzyldimethylhexadecylammonium cholate; methyl 1,3-dihydroxycholan-24-oate; and trioctylmethylammonium cholate); cholic acid glucuronide; cholyl-coenzyme A; cholyllysylfluorescein; cholyldiglycylhistamine; cholylhistamine; cholylhydroxamic acid; cholylsarcosine; cholyltetraglycylhistamine; ciliatocholic acid; dehydrocholic acid (which includes FZ 560; Gallo-Merz; Gillazym; Hepavis; Mexase; progresin Retard; and spasmocanulase);

23-nordeoxycholic acid; 3,7-dioxocholanoic acid; 3-hydroxy-polydeoxycholic acid; 3-sulfodeoxycholic acid; 6-hydroxycholanoic acid; 6-methylmurideoxycholic acid; 7-ketodeoxycholic acid; 7-methyldeoxycholic acid; chenodeoxycholic acid; dehydrodeoxycholic acid; deoxycholyltyrosine; desoxybilianic acid; glycodeoxycholic acid; hyodeoxycholate-6-O-glucuronide; hyodeoxycholic acid; taurodeoxycholic Acid; and ursodeoxycholic acid; glycocholic acid; 3-hydroxy-5- cholenoylglycine; cholylglycylhistamine; cholylglycyltyrosine; glycodeoxycholic Acid; sulfolithocholylglycine; hemulcholic acid; 12-ketolithocholic acid; 24-norlithocholic acid; 3-dehydrolithocholylglycine; 3-hydroxy-6-cholen-24-oic acid; 3-hydroxy-7,12-diketocholanoic acid; 3-hydroxy-7-methylcholanoic acid; 3-ketolithocholic acid; 3-oxochol-4-en-24-oic acid; 3-oxocholan-24-oic acid; 4-azidophenacyl lithocholate; 7-ketolithocholic acid; BRL 39924A; glycolithocholic acid; lithocholate 3-O-glucuronide; lithocholyl-N-hydroxysuccinimide; methyl lithocholate; N-carbobenzoxy-N-lithocholyl-epsilon-lysine; N-epsilon-lithochoiyllysine; sulfolithocholic acid; and taurolithocholic acid; muricholic acid; N-(1,3,7,12-tetrahydroxycholan-24-oyl)-2-aminopropionic acid; N-(2-aminoethyl)-3,7,12-trihydroxycholan-24-amide; N-carboxymethyl)-N-(2-(bis(carboxymethyl)amino)ethyl)-3-(4-(N'-(2-((3,7,12-trihydroxycholan-24-oyl)araino)ethyl)(thioureido) phenyl)alanine; N-cholyl-2-fluoro-beta-alanine; norcholic acid; norursocholic acid; taurocholic acid; (N-(7-(nitrobenz-2-oxa-1,3-diazol-4-yl))-7-amino-3alpha,12alpha-dihydroxycholan-24-oyl)-2-aminoethanesulfonate; 23-seleno-25-homotaurocholic acid; 3,12-dihydroxy~7~oxocholanoyltaurine; 3-hydroxy-7-oxocholanoyltaurine; azidobenzamidotaurocholate; hexadecyltributylammonium taurocholate; tauro 1-hydroxycholic acid; tauro-3,7- dihydroxy-12-ketocholanoic acid; taurodehydrocholate; taurodeoxycholic acid; tauroglycocholic acid; taurolithocholic acid; tauromurichoUc acid; tauronorcholic acid); tetrahydroxy-5-cholan-24-oic acid; ursocholic acid; vulpecholic acid; bile acid sulfates; glycodeoxycholic acid; glycochenodeoxycholic acid; 7-oxoglycochenodeoxycholic acid; glycochenodeoxycholate-3-sulfate; glycohyodeoxycholic acid; tauro-7,12-dihydroxycholanic acid; taurochenodeoxycholic acid; taurochenodeoxycholate-3-sulfate; taurochenodeoxycholate-7-sulfate; tauroursodeoxycholic acid; taurohyodeoxycholic acid; the includes: 23-methylursodeoxycholic acid; 24-norursodeoxycholic acid; 3,6-di-hj?droxy-6-methylcholanoic acid; 3,7-dihydroxy-20,22-methylenecholan-23-oic acid; 3,7-dihydroxy-22,23-methylenecholan-24-oic acid; 3,7-dihydroxy-7-ethylcholanoic acid; 3,7-dihydroxy-7-methylcholanoic acid; 3,7-dihydroxy-7-n-propylcholanoic acid; Bamet-UD2; diammhiebis(ursodeoxycholate(O,O'))pIatinum(II); glycoursodeoxycholic acid; homoursodeoxycholic acid; HS 1030; HS 1183; isoursodeoxycholic acid; PABA-ursodeoxycholic acid; sarcosyl-sarcoursodeoxycholic acid; sarcoursodeoxycholic acid; ursodeoxycholate-3-sulfate; ursodeoxycholic acid 7-oleyl ester; ursodeoxycholic acid N-acetylglucosaminide; ursodeoxycholic acid-3-O-glucuronide; ursodeoxycholyl N-carboxymethylglycine; ursodeoxycholylcysteic acid; ursometh; 24-norchenodeoxycholic acid; 3,7-dihydroxy-12-oxocholanoic acid; 3,7-dihydroxy-24-norcholane-23-sulfonate; 3,7-dihydroxy-25-homocholane-25-sulfonate; 3,7-dihydroxy-chol-5-enoic acid; 3,7-dihydroxycholane-24-sulfonate; 3-glucosido-chenodeoxycholic acid; 3-oxo-7-hydroxychol-4-enoic acid; 6-ethylchenodeoxycholic acid; chenodeoxycholate sulfate conjugate; chenodeoxycholyltyrosine; glycochenodeoxycholic acid which includes: 7-oxoglycochenodeoxycholic acid and glycochenodeoxycholate-3-sulfate; homochenodeoxycholic acid; HS 1200; methyl 3,7-dihydroxychol-4-en-24-oate; methyl 3,7-dihydroxycholanate; N-(2-aminoethyl)-3,7-dihydroxycholan-24-amide; N-chenodeoxycholyl-2-fluoro-beta-alanine; sarco-chenodeoxycholic acid; taurochenodeoxycholic acid; taurochenodeoxycholate-3-sulfate; taurochenodeoxycholate-7-sulfate; tauroursodeoxycholic acid.

Examples of Saponin Emulsifiers

In some embodiments, saponins are provided as emulsifiers. Saponins are naturally occurring compounds predominantly derived from plants and which have detergent properties. The name saponin is derived from the soapwort plant (*Saponaria*) traditional used in the making of a type of soap. Saponins are the glycosides of 27 carbon steroids or 30 carbon triterpenes. Removal of the sugar moiety from a saponin by hydrolysis yields the aglycone, sapogenin. Triterpenoid saponins are generally acid, while steroid saponins are generally neutral.

Steroid saponins include three classes of compounds, the cholestanol, furostanol, and spirostanol saponins. Examples of furostanol saponins can include, protoisoeruboside-B and isoeruboside-B, as well as saponins derived, for example, from *Ruscus aculeatus, Tacca chantrieri, Solanum hispidum, Dioscorea polygonoides, Tribulus terrestris*, and *Lilium candidum*. Other steroid saponins can include those derived from *Saponaria officinalis, Yucca schidigera*, and *Chlorogalum pomeridianum*.

Examples of triterpenoid saponins can include those of the fusidane-lanostante group, cyclopassiflosides, cycloglobiseposides, cycloartanes, dammaranes (e.g., bacopasaponin and jujubogenin), lupanes (e.g., quadranosides), oleananes (e.g., maesapinin), ligatosides, sandrosaponins, pedunsaponins), vulgarsaponin, peduncularisaponin, petersaponin, araliasaponin, assamsaponin, eupteleasaponin, herniariasaponin, jeosaponin, meliltussaponin, ursanes (e.g., randisaponins), brevicuspisaponin, ursolic acid, and indicasaponin. Triterpenoids can also be derived from *Quillaja saponaria*, as well as those derived from grapes.

Saponins have been identified in plants and animals including, for example, and without being limiting, agave, alfalfa, aloe, *Anadenanthera peregrine*, amaranth, *Angelica sinesis, Aralia chinesis, Aralia manshurica*, asparagus, *Astragalus membranaceus, Bacopa monnieri, Boussingaultia* sp., *Bupleurum chinense, Calendula officinalis, Capsicum* sp., chickweed, *Chlorophytum* sp., *Chlorogalum* sp., *Codonopsis pilosula*, horse chestnuts, curcurbit, *Digitalis* sp., *Echinodermata*, Elecampane, *Elutherococcus senticosus*, fenugreek, goldenrod, gotu kola, grape skin, *Gymnema sylvestre, Gypsophila* sp., hawthorn, jiaogulan, licorice, lungwort, mullein, olives, onion, pannax (Koren Ginseng), *Platycodon grandiflorum, Polygala tenuifola, Quillaja saponaria*, quinoa, *Phytolacca americana*, rambutan, *Salvia* sp., soapberry, *Saponaria* sp., *Schizandra chinensis*, shallots, southern pea, soybean, *Tribulus terrestris*, wild yam, yucca, and *Zizyphus jujube*.

Examples of Detergents

Various detergents are useful as emulsifiers in embodiments as described herein, including ionic detergents, nonionic detergents, and zwitterionic detergents. Detergents can be used to augment or enhance the effectiveness of other emulsifiers such as bile acids and/or saponins. Detergent can also be used as permeability enhancers, effective to enhance the permeability of membranes or tissue to emulsifiers.

Examples of Routes of Administration

Various routes of administration of emulsifiers can be used, for example, and without being limiting, by injection, transdermally, orally, by inhalation, and transmucosally. In some embodiments, emulsifiers can be perfused directly into the systemic circulation by way of an implantable pump. Regardless of the route of administration, the dosing of emulsifiers will result in achieving sustained levels of an emulsifier in the systemic circulation that are effective to result in plaque regression.

In some embodiments, formulations comprise a sustained release formulation that results in the maintenance of circulating levels of emulsifiers that are effective to result in plaque regression. In some embodiments, formulations can comprise a sustained release delivery system can be used to deliver the emulsifier such that increased levels are achieved for extended periods of time, for example, a period of 2 hours or longer. In some embodiments, release is sustained over a period of 24 hours. In some embodiments, a sustained release delivery system can further comprise one or more pharmaceutical diluents known in the art. Exemplary pharmaceutical diluents include, without limitation, monosaccharides, disaccharides, polyhydric alcohols and a combination thereof. In some embodiments, pharmaceutical diluents can include, for example, starch, lactose, dextrose, mannitol, sucrose, microcrystalline cellulose, sorbitol, xylitol, fructose, a combination thereof.

In some embodiments, the pharmaceutical diluent can be water-soluble, for example, lactose, dextrose, mannitol, sucrose, and a combination thereof. In some embodiments, the sustained release delivery system can comprise one or more pharmaceutical diluents in an amount of about 5% to about 80% by weight; from about 10% to about 50% by weight; or about 20% by weight of a dosage form.

In some embodiments, a emulsifier delivery system can comprise one or more hydrophobic polymers. The hydrophobic polymers can be used in an amount sufficient to slow the hydration of the active ingredients. For example, the hydrophobic polymer can be present in the sustained release delivery system in an amount of about 0.5% to about 20% by weight; in an amount of about 2% to about 10% by weight; in an amount of about 3% to about 7% by weight; or in an amount of about 5% by weight.

Embodiments of formulations as described herein can be admixed with one or more wetting agents (e.g., polyethoxylated castor oil, polyethoxylated hydrogenated castor oil, polyethoxylated fatty acid from castor oil, polyethoxylated fatty acid from hydrogenated castor oil, or a combination thereof) one or more lubricants (e.g., magnesium stearate, sodium stearyl fumarate), one or more glidants (e.g., silicon dioxide), one or more buffering agents, one or more colorants, and/or other conventional ingredients well known to those of skill in the art of pharmaceutical compounding.

In some embodiments, a sustained release coating can comprise at least one water insoluble compound, for example, a hydrophobic polymer. The hydrophobic polymer can be the same as or different from the hydrophobic polymer used in the sustained release delivery system. Exemplary hydrophobic polymers include, without being limiting, alkyl celluloses (e.g., $C_{1-6}$ alkyl celluloses, carboxymethylcellulose), other hydrophobic cellulosic materials or compounds (e.g., cellulose acetate phthalate, hydroxypropylmethylcellulose phthalate), polyvinyl acetate polymers (e.g., polyvinyl acetate phthalate), polymers or copolymers derived from acrylic and/or methacrylic acid esters, zein, waxes (alone or in admixture with fatty alcohols), shellac, hydrogenated vegetable oils, and a combination thereof. In some embodiments, the hydrophobic polymer can comprise methyl cellulose, ethyl cellulose, propyl cellulose or a mixture of two or more thereof. In another embodiment, the hydrophobic polymer is ethyl cellulose. The compositions of the invention can be coated with a water insoluble compound to a weight gain from about 1 to about 20% by weight.

Formulation can be coated with a sustained release coating that can further comprise at least one plasticizer such as triethyl citrate, dibutyl phthalate, propylene glycol, polyethylene glycol, or mixtures of two or more thereof. A sustained release coating can also contain at least one water soluble compound, such as polyvinylpyrrolidones, hydroxypropylmethylcelluloses, and mixtures thereof.

A sustained release coating can be applied to a core comprising one or more emulsifiers by spraying an aqueous dispersion of the water insoluble compound onto core. The core can be a granulated composition made, for example, by dry or wet granulation of mixed powders of emulsifiers and at least one binding agent; by coating an inert bead with emulsifiers and at least one binding agent; or by spheronizing mixed powders of emulsifiers and at least one spheronizing agent. Some exemplary binding agents include hydroxypropylmethylcelluloses. Exemplary spheronizing agents can include microcrystalline celluloses. The inner core can be a tablet made by compressing the granules or by compressing a powder comprising emulsifiers and/or pharmaceutically acceptable salts or conjugates thereof.

In some embodiments, the compositions comprising emulsifiers and a sustained release delivery system, as described herein, are coated with a sustained release coating, as described herein. In some embodiments, the compositions comprising emulsifiers and a sustained release delivery system, as described herein, are coated with a hydrophobic polymer, as described herein. In some embodiments, the compositions comprising emulsifiers and a sustained release delivery system, as described herein, are coated with an enteric coating. Exemplary enteric coatings include, without being limiting, cellulose acetate phthalate, hydroxypropylmethylcellulose phthalate, polyvinylacetate phthalate, methacrylic acid copolymer, shellac, hydroxypropylmethylcellulose succinate, cellulose acetate trimelliate, and a combination thereof.

In some embodiments, the compositions comprising an emulsifier and a sustained release delivery system, as described herein, are coated with a hydrophobic polymer, as described herein, and further coated with an enteric coating. In any of the embodiments described herein, the compositions comprising emulsifiers and a sustained release delivery system, as described herein, can optionally be coated with a hydrophilic coating which can be applied above or beneath a sustained release film, above or beneath the hydrophobic coating, and/or above or beneath the enteric coating. Exemplary hydrophilic coatings include hydroxypropylmethylcelluloses.

Formulations can further comprise agents to enhance absorption across the intestinal epithelium. These can include, without being limiting, other emulsifiers or detergents, some of which are listed above, EDTA, sodium salicylate, sodium caprate, diethyl maleat, N-lauryl-β-D-maltophyranoside, linoleic acid polyoxyethylated, tartaric acid, SDS, Triton X-100, hexylglucoside, hexylmaltoside, heptylglucoside, octylglucoside, octylmaltoside, nonylglucoside, nonylmaltoside, decylglucoside, deceylmaltoside, dodecylmaltoside, tetradecylmaltoside, dodecylglucoside, tridecylmaltoside, as well as mucolytic agents, for example N-acetylcysteine and chitosan.

Where a transdermal route is selected, the formulation can further comprise one or more permeability enhancers, effective to increase the rate of movement of the emulsifier across the epithelium and into the systemic circulation. Permeability enhancers can include, for example, sulfoxides, alcohols, fatty acids and fatty acid esters, polyols, surfactants, terpenes, alkanones, liposomes, ethosomes, cylodextrins. In some embodiments permeability enhancers include, without being limiting, ethanol, glyceryl monoethyl ether, monoglycerides, isopropylmyristate, lauryl alcohol, lauric acid, lauryl lactate, lauryl sulfate, terpinol, menthol, D-limonene, DMSO, polysorbates, N-methylpyrrolidone, polyglycosylated glycerides, Azone®, CPE-215®, NexAct®, SEPA®, and phenyl piperizine.

In some embodiments other methods of administration across an epithelium can be used, for example, iontophoresis, electroporation, sonophoresis, thermal poration, microneedle treatment, and dermabrasion.

In some embodiments, the pharmaceutical formulation is administered so as to achieve circulating levels of at least 50 µM of the emulsifier within 5 minutes after administration. In some embodiments, administration is performed intravenously. In some embodiments, administration occurs intraarterially. In some embodiments, levels in a range from about 50 µM to about 600 µM are achieved within 5 minutes of administration. In some embodiments, levels in a range from about 100 µM to about 600 µM are achieved within 5 minutes of administration. In some embodiments, levels in a range from about 100 µM to about 300 µM are achieved within 5 minutes of administration.

Combinations of Emulsifiers and Statins

In some embodiments, a method of treating a patient having, or suspected of having, atherosclerotic plaques can include treatment with an emulsifier as described above, in combination with agents that are effective to lower cholesterol. For example, the class of compounds known as "statins" are effective to lower cholesterol. Statins are inhibitors of HMG-CoA reductase, the rate limiting enzyme in the synthesis of mevalonate, a key intermediate in the synthesis of cholesterol, from acetyl-CoA.

A variety of natural and synthetic statins are known. These include, for example and without being limiting, atorvastatin, cerivastatin, fluvastatin, lovastatin, mevastatin, pitavastatin, pravastatin, rosuvastatin, and simvastatin. Therefore, in some embodiments, a method of treating atherosclerosis, effective to result in a reduction in plaque volume can comprise treatment with an emulsifier as described above effective to achieve a level of the administered emulsifier in the systemic circulation, greater than about 50 uM, in combination with a statin. In some cases, the statin can be administered at a dosage of 20 mg/day; in some cases the statin can be administered at a dosage of 40 mg/day. The statin and emulsifier can be administered concurrently, or sequentially. In some embodiments, the statin and emulsifier can be provided in the same pharmaceutical composition, either as a mixture or in sub-compartments of a single dosage form such as a pill, capsule, injectable, or any other suitable form for administration.

In some embodiments, emulsifiers can be administered in combination with a statin and an agent effective to control blood pressure. For example, in some cases emulsifiers can be provided simultaneously, or sequentially, with a statin and a compound like amlodipine.

Emulsifiers, as well as other therapeutic compounds, for example, statins, can be administered by way of a stent. In some embodiments, after an angioplasty procedure, a stent comprising at least one emulsifier as described above, can be placed in a vessel at the site of the angioplasty. The stent is configured to release the emulsifiers in a sustained fashion, such that a local concentration that is effective to dissolve plaques is achieved. The stent can be loaded with one or more emulsifiers, and/or additional therapeutic compounds, and configured to release the therapeutic ingredients over an extended period of time. In some embodiments, the local concentration of emulsifier provided by the stent can be greater than 50 µM. In some embodiments, the local concentration of emulsifier can be in a range from about 50 µM to about 600 µM. In some embodiments, the local concentration of the emulsifier can range from about 100 µM to about 300 µM. Emulsifier eluting stents can be of a balloon-expandable design, or self-expanding. The stent can also include additional agents effective to dissolve plaque, for example, ionic detergents, nonionic detergents, and zwitterionic detergents. An exemplary list of detergents is provided in International Application PCT/US2007/001214, the entire contents of which are incorporated by reference herein.

In some embodiments, a stent can further comprise enzymes that will digest other components of the plaque (e.g., the fibrous cap), for example proteolytic enzymes such as collagenase, Pronase, Proteinase K, trypsin, chymotrpysin, and other proteases well known to those in the art. Proteases can be selected from classes of proteases including, and without being limiting, serine proteases, threonine proteases, cysteine proteases, aspartic acid proteases, metalloproteases, and glutamic acid proteases. As such, the enzymes listed are understood to be merely exemplary and not exhaustive of the enzymes that can be included in a stent configured for sustained release of emulsifiers. Proteolytic enzymes that are effective to dissolve blood clots, can also be useful in embodiments of stents that release emulsifiers, in order to prevent, or at least limit, the risk of forming a thrombus at or near the site where the stent is placed in the patient. A stent can also include other therapeutic agents such as anti-inflammatory compounds, or compounds that are effective to promote healing of the vessel.

Experimental Examples

In vitro experiments were performed to test the ability of deoxycholic acid (DCA) to solubilize atherosclerotic plaque material. In these experiments, ex vivo samples of pig artery were bathed in an aqueous solution at two different concentrations of DCA. In the first experiment, samples were treated with 50 mg/mL DCA for successive periods of 30 minutes, at which time the sample was removed from the bathing medium, and the appearance of the plaque examined macroscopically. Early in the treatment, on removal of the sample from the bath a clear, viscous, column of fluid extended from the sample. This column of fluid continued to be apparent when samples were evaluated up to about 4 or 5 hours, after which the fluid column was no longer noted. Without wishing to be held to any one theory of operation, it was concluded that the clear fluid comprised components of the plaque.

After 5 hours of treatment with DCA, macroscopic assessment of plaque size suggested that plaque volume had decreased by about 70%. After 36 hours of exposure all that appeared to remain of plaques were the fibrous cap material and areas of calcification. All core material appeared to have been solubilized.

In a second experiment, atherosclerotic plaque in a sample of pig artery was exposed to a continuous flow of a solution of 0.25 mg/mL DCA, diluted in normal saline (approximately 600 µM DCA). The sample was continuously exposed for a period of 8 days. Macroscopic examination of the sample at this time revealed that most, if not all, of the lipid core of the plaque had been solubilized, and all that remained was the fibrous cap.

In both experiments, treatment with DCA caused no obvious detrimental effects on the vessel itself. In particular, elasticity of the vessel wall appeared unaffected. While not wishing to be held to any one theory of operation, sustained levels of an emulsifier are demonstrated by this example to be effective to produce regression of atherosclerotic plaque, apparently by dissolving the lipid components of the plaque, which once solubilized cross the fibrous cap into the surrounding milieu. In a patient, it is expected that solubilized lipid liberated from plaques by the administered emulsifiers, will be released into the blood stream where they can be metabolized and eliminated from the body by normal physiological routes, for example, by excretion in the bile as free cholesterol, or by conversion to bile acids in the liver.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. A method of treating atherosclerosis in a patient in need thereof comprising:
   administering a pharmaceutical formulation comprising a bile acid consisting of hyodeoxycholic acid, its pharmaceutically acceptable salt, hydrate, solvate or polymorph in an amount effective to achieve a concentration of the hyodeoxycholic acid in the systemic circulation of greater than 50 $\mu$M;
   wherein the concentration of the hyodeoxycholic acid in the systemic circulation is sustained for a period of at least two hours;
   wherein the concentration of the hyodeoxycholic acid is effective to result in regression of an atherosclerotic plaque.

2. The method of claim 1, wherein the formulation further comprises at least one of a saponin, a detergent, and mixtures thereof.

3. The method of claim 1, wherein the sustained levels of the bile acid in the systemic circulation are in a range between about 50 $\mu$M and about 600 $\mu$M.

4. The method of claim 1, wherein the sustained levels of the bile acid in the systemic circulation are in a range between about 100 $\mu$M and about 300 $\mu$M.

5. The method of claim 1, further comprising using a permeability enhancer.

6. The method of claim 5, wherein the permeability enhancer comprises at least one of a non-ionic detergent, an ionic detergent, and a zwitterionic detergent.

7. The method of claim 1, further comprising administering a statin either simultaneously or sequentially with the pharmaceutical formulation.

8. The method of claim 7, wherein the pharmaceutical formulation further comprises the statin.

9. A method of treating atherosclerosis in a patient in need thereof comprising:
   administering a pharmaceutical formulation comprising a bile acid consisting of hyodeoxycholic acid, its acceptable salt, hydrate, solvate, or polymorph in an amount effective to achieve a concentration of the hyodeoxycholic acid in the systemic circulation of greater than 50 $\mu$M at five minutes after the onset of administration;
   wherein the concentration of the hyodeoxycholic acid in the systemic circulation is sustained above 50 $\mu$M for a period of at least two hours; and
   wherein the concentration of the hyodeoxycholic acid is effective to result in regression of an atherosclerotic plaque.

10. The method of claim 9, wherein the sustained levels of the bile acid in the systemic circulation are in a range between about 50 $\mu$M and about 600 $\mu$M.

11. The method of claim 9, wherein the sustained levels of the bile acid in the systemic circulation are in a range between about 100 $\mu$M and about 300 $\mu$M.

* * * * *